(12) United States Patent     (10) Patent No.:     US 12,678,539 B2
You                              (45) Date of Patent:        Jul. 14, 2026

(54) METHOD OF MANUFACTURING A TISSUE REGENERATION PATCH

(71) Applicant: ROKIT HEALTHCARE INC., Seoul (KR)

(72) Inventor: Seok Hwan You, Seoul (KR)

(73) Assignee: ROKIT HEALTHCARE INC., Seoul (KR)

( * ) Notice: Subject to any disclaimer, the term of this patent is extended or adjusted under 35 U.S.C. 154(b) by 756 days.

(21) Appl. No.: 17/754,323

(22) PCT Filed: Dec. 24, 2021

(86) PCT No.: PCT/KR2021/019803
§ 371 (c)(1),
(2) Date: Mar. 30, 2022

(87) PCT Pub. No.: WO2022/139540
PCT Pub. Date: Jun. 30, 2022

(65) Prior Publication Data
US 2024/0042100 A1     Feb. 8, 2024

(30) Foreign Application Priority Data

Dec. 24, 2020     (KR) ........................ 10-2020-0183901

(51) Int. Cl.
*A61L 27/36*     (2006.01)
*A61L 27/60*     (2006.01)

(52) U.S. Cl.
CPC ....... *A61L 27/3604* (2013.01); *A61L 27/3691* (2013.01); *A61L 27/60* (2013.01); *A61L 2430/34* (2013.01); *A61L 2430/40* (2013.01)

(58) Field of Classification Search
CPC .. A61L 27/3604; A61L 27/3691; A61L 27/60; A61L 2430/34; A61L 2430/40; A61L 27/36; A61L 27/56; A61B 34/10; A61B 2034/105; A61B 2034/108; A61F 2/10; A61F 2/105; A61F 2240/004
See application file for complete search history.

(56) References Cited

U.S. PATENT DOCUMENTS

| | | | | |
|---|---|---|---|---|
| 2019/0232558 A1* | 8/2019 | You | ........................ | B29C 64/386 |
| 2021/0030926 A1* | 2/2021 | You | ........................ | B33Y 70/10 |
| 2021/0038762 A1* | 2/2021 | You | ........................ | A61L 27/227 |
| 2021/0401897 A1* | 12/2021 | You | ........................ | A61K 35/44 |

FOREIGN PATENT DOCUMENTS

| | | | | |
|---|---|---|---|---|
| CN | 106693080 B | 4/2020 | | |
| JP | 5789799 B2 * | 10/2015 | ........... | A61L 27/227 |
| KR | 101710615 B1 | 2/2017 | | |
| KR | 10-2019-0098907 A | 8/2019 | | |
| KR | 102091151 B1 | 3/2020 | | |
| WO | 2005-011569 A2 | 2/2005 | | |
| WO | WO-2012019103 A2 * | 2/2012 | ........ | A61M 5/14526 |
| WO | WO-2019151597 A1 * | 8/2019 | ......... | A61F 2/30756 |
| WO | WO-2019151611 A1 * | 8/2019 | ............. | A61K 38/57 |

OTHER PUBLICATIONS

Bide (https://www.sciencedirect.com/topics/medicine-and-dentistry/polyurethan, first paragraph, 2006 (Year: 2006).*
JP5789799B2—machine english translation from google, 2015, accessed Oct. 5, 2024, no pagination.*
International Search Report in Application No. PCT/KR2021/019803, issued on Apr. 12, 2022, 13 pages.
Written Opinion in Application No. PCT/KR2021/019803, issued on Apr. 12, 2022, 4 pages.

* cited by examiner

*Primary Examiner* — Monica A Shin
(74) *Attorney, Agent, or Firm* — Osha Bergman Watanabe & Burton LLP

(57) ABSTRACT

The present invention method for manufacturing a tissue regeneration patch includes: A) preparing a micronized adipose tissue extract; B) injecting the micronized adipose tissue extract into a mold of a predetermined shape; C) cooling the mold into which the adipose tissue extract is injected at a temperature between −25° C. and −10° C.; and D) removing the mold to obtain a tissue regeneration patch.

10 Claims, 4 Drawing Sheets

[FIG. 1]
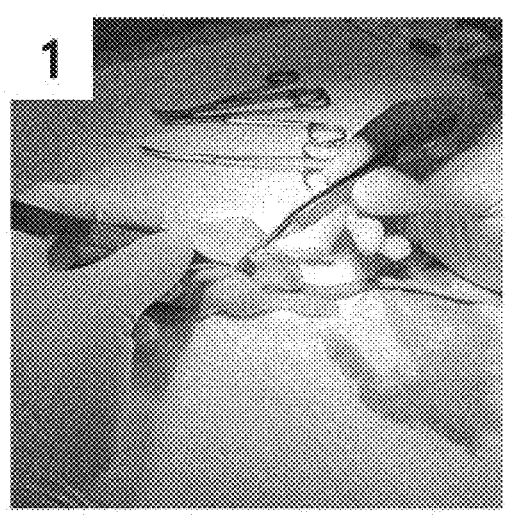
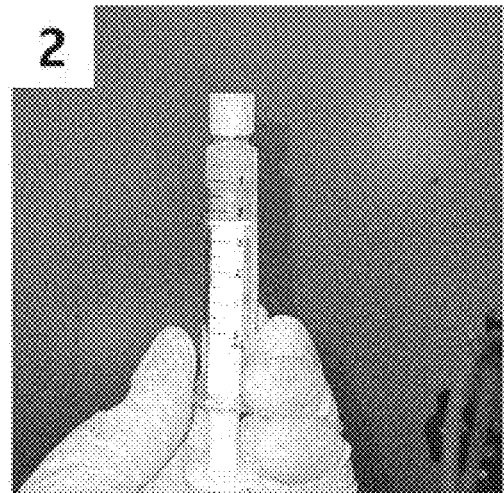
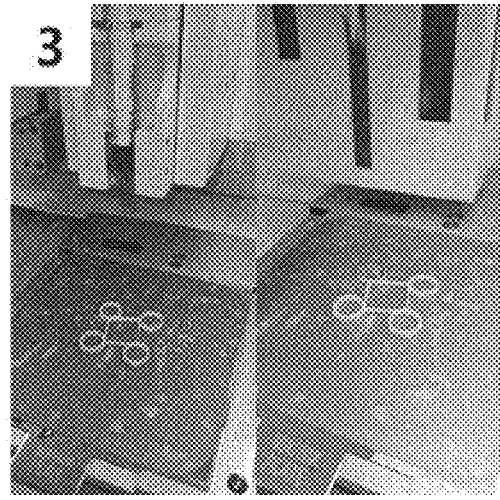

[FIG. 2]
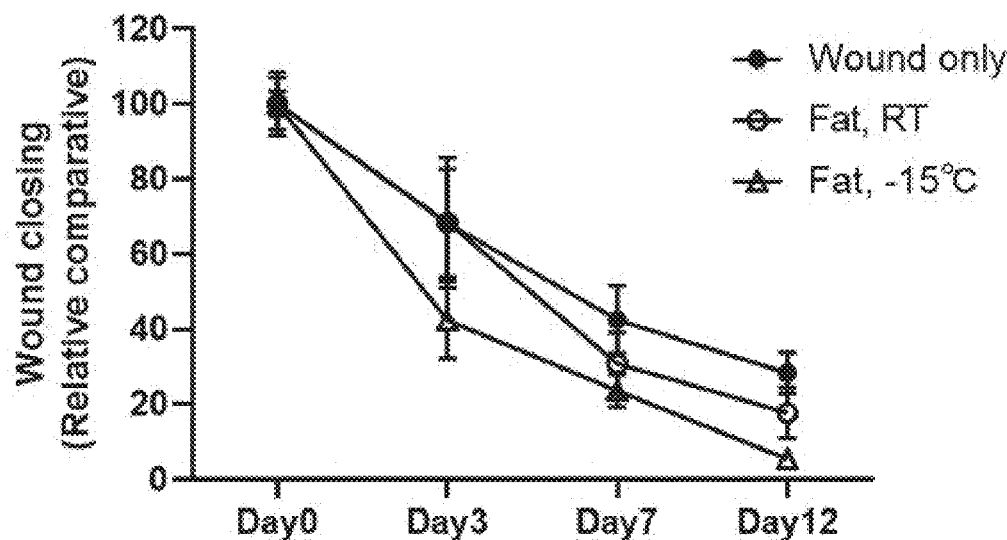

[FIG. 3]
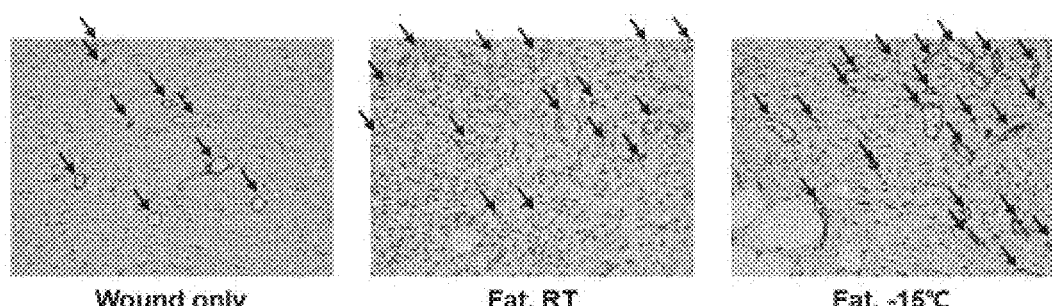
[FIG. 4]
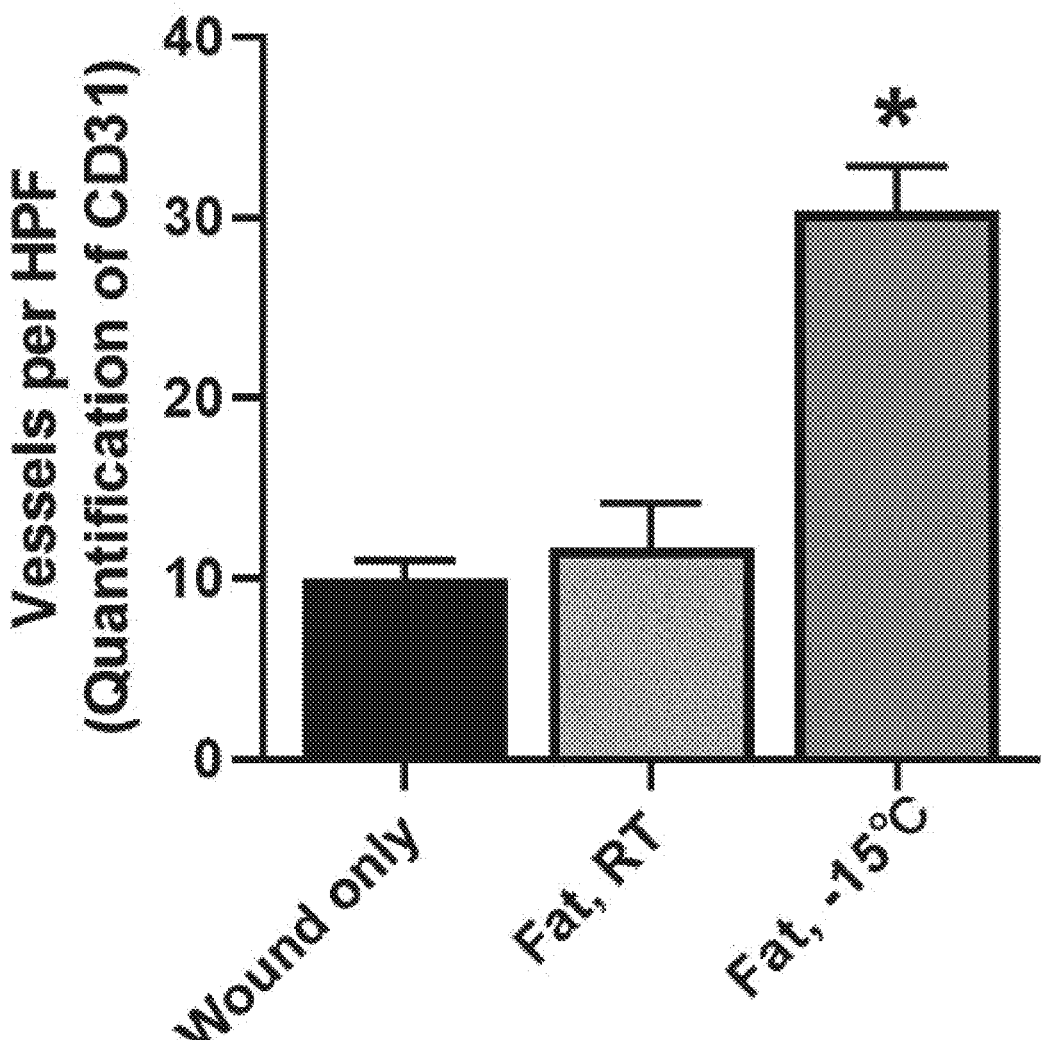

[FIG. 5]
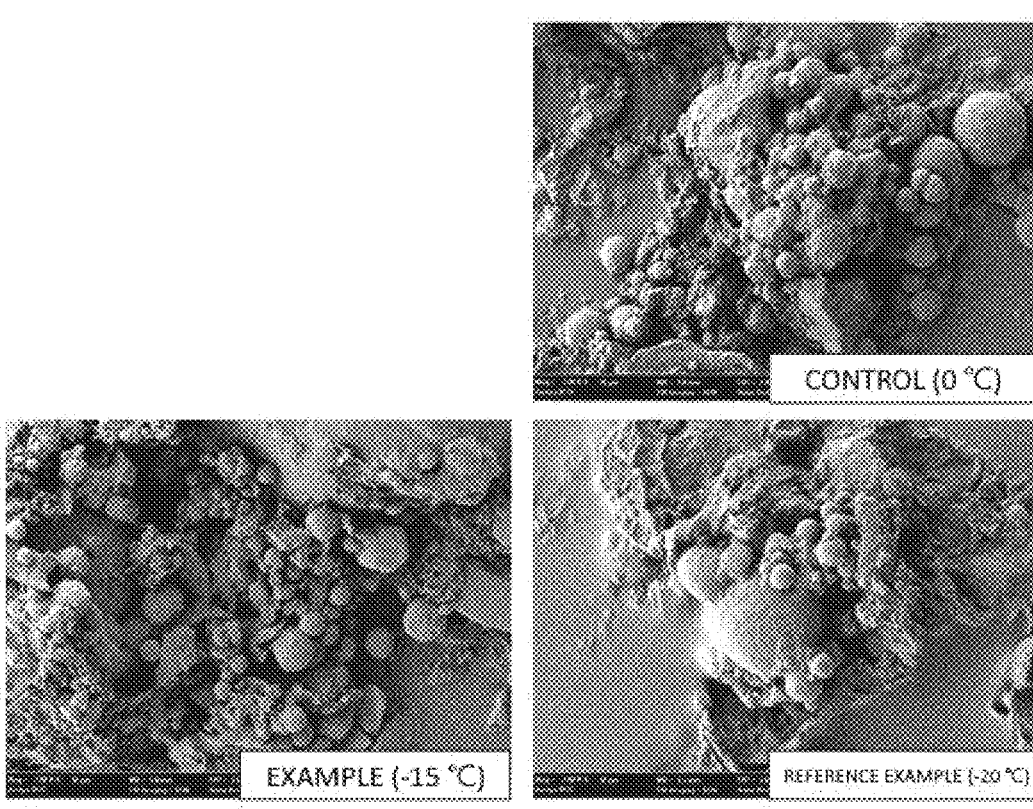

METHOD OF MANUFACTURING A TISSUE REGENERATION PATCH

TECHNICAL FIELD

This specification claims the benefit of the filing date of Korean Patent Application No. 10-2020-0183901 filed with the Korean Intellectual Property Office on Dec. 24, 2020, the entire contents of which are incorporated herein by reference.

The present invention relates to a method for manufacturing a tissue regeneration patch. Specifically, it relates to a method of manufacturing a tissue regeneration patch customized for damaged or lost tissue.

BACKGROUND ART

In particular, diabetic foot disease refers to a foot ulcer caused by tearing of skin tissue caused by a skin wound on the foot of a person with diabetes. This is a phenomenon that occurs when neuropathy or a peripheral vascular disease caused by diabetes causes ulcers on the feet of diabetic patients or worsens wound infection. About 20% of patients with diabetes will undergo at least one incidence of diabetic foot disease, of which about 1-3% will undergo surgery to amputate a part of the leg. In addition, it is known that more than half of the cases of leg amputation, except for cases due to trauma, are due to diabetic foot disease.

A skin burn can be defined as a thermal attack on the skin. Skin burns can cause partial or total destruction of the skin, soft tissues, ears and eyes, hair and body hair, nails and even bones. Most burns affect only the skin, namely the epidermis and dermis. However, in the case of third-degree burns, it causes total destruction or vitrification of the epidermis and dermis, and this type of burn often damages subcutaneous tissues such as blood vessels, muscles and nerves. To treat this type of burn, it is customary to perform a skin graft because it is theoretically possible that no scarring of the epidermis is formed. Furthermore, fourth-degree burns affect muscles and can even extend to bones. In this case, the appearance of the skin is said to be carbonized, and the recommended treatment may be amputation.

As such, diabetic foot disease or skin damage due to burns is a very important causes that could reduce a patient's quality of life, and much research is needed to come up with ways to regenerate necrotic skin tissues and restore normal life for patients.

RELATED ART LITERATURE

Patent Literature

Republic of Korea Patent Registration No. 10-1710615.

DISCLOSURE

Technical Problem

The objective of the present invention is to provide a method for manufacturing a tissue regeneration patch capable of treating a damaged or lost tissue. Specifically, it relates to a method of manufacturing a tissue regeneration patch tailored to a damaged or lost tissue, in particular, damaged or lost skin tissue due to diabetic foot disease and burns.

Technical Solution

One embodiment of the present invention describes a method of manufacturing a tissue regeneration patch including: A) preparing a micronized adipose tissue extract; B) injecting the micronized adipose tissue extract into a mold of a predetermined shape; C) cooling the mold into which the adipose tissue extract is injected at a temperature between −25° C. and −10° C.; and D) removing the mold to obtain a tissue regeneration patch.

Another embodiment of the present invention describes the direct provision of a tissue regeneration patch that has been manufactured using the aforementioned manufacturing method.

Advantageous Effects

The method for manufacturing a tissue regeneration patch according to the present invention yields a tissue regeneration patch capable of simple and rapid tissue treatment. In particular, the method for manufacturing a tissue regeneration patch according to the present invention can rapidly manufacture a customized tissue regeneration patch at the site of clinical intervention. Furthermore, the tissue regeneration patch produced by the manufacturing method according to the present invention can promote effective skin regeneration, particularly in damaged or lost skin areas of patients with diabetic foot disease or burns.

DESCRIPTION OF DRAWINGS

FIG. 1 is a set of photographs sequentially showing the manufacturing process of the tissue regeneration patch according to the embodiment and application of the tissue regeneration patch to the affected area.

FIG. 2 is a graph obtained from measuring the size of the affected area on the 3rd, 7th, and 12th day after the dressing treatment in Example 1, Comparative Examples 1 and 2, respectively.

FIG. 3 shows the results of neovascularization in the recovered affected area in Example 1, Comparative Examples 1 and 2, respectively.

FIG. 4 is a graph of the result of FIG. 3.

FIG. 5 is an image of a tissue regeneration sheet according to a Reference Example observed using a scanning electron microscope.

MODES OF THE INVENTION

Throughout the specification, when a portion is said to "include" a component, this means that other components may be further included, rather than excluded, unless specifically stated to the contrary.

In the present specification, when a member is said to be located "on" another member, this includes not only a case in which a member is in contact with another member but also a case in which another member is present between the two members.

Hereinafter, the present invention will be described in detail.

One embodiment of the present invention provides a method for manufacturing a tissue regeneration patch, including: A) preparing a micronized adipose tissue extract;
  B) injecting the micronized adipose tissue extract into a mold of a predetermined shape;
  C) cooling the mold into which the adipose tissue extract is injected at a temperature range between −25° C. and −10° C.; and
  D) removing the mold to obtain a tissue regeneration patch.

The tissue regeneration patch according to the present invention has the advantage that it can be manufactured by a simple method. In particular, it is possible to easily provide a patient-specific tissue regeneration patch by using 2D or 3D scan data of the affected area, and furthermore, it is possible to quickly perform the steps from adipose tissue extraction to the manufacture of a tissue regeneration patch directly at the site of clinical intervention.

Step A): Preparing a Micronized Adipose Tissue Extract

According to one embodiment of the present invention, the micronized adipose tissue extract may be prepared using the extracted adipose tissue. Specifically, the micronized adipose tissue extract may be obtained by extracting adipose tissue using a general liposuction technique and then micronizing it.

According to one embodiment of the present invention, the adipose tissue may be autologous adipose tissue. Specifically, the adipose tissue may be the patient's autologous adipose that may be extracted through liposuction. In addition, the adipose tissue may be obtained by extracting the adipose tissue using liposuction and then removing at least a portion of physiological saline and blood mixed with the adipose tissue. Specifically, the adipose tissue can be obtained by leaving the extract obtained using liposuction for a predetermined duration of time to remove the blood and physiological saline layer separated from the adipose layer. In this way, when physiological saline and blood are removed, the following adipose tissue extract may be more effectively extracted, and the prepared adipose tissue extract may more effectively include growth factors and active cells suitable for treatment.

According to an embodiment of the present invention, step A) may include the step of pulverizing the adipose tissue in stages sequentially using a1) a first filter having a pore diameter of 2 mm to 5 mm, a second filter having a pore diameter of 400 μm to 800 μm, and a third filter having a pore diameter of 150 μm to 250 μm.

According to one embodiment of the present invention, the first to third filters may be micronizers. In addition, the first to third filters are syringe filters, and adipose tissue may be pulverized by passing the adipose tissue through the filter in syringe. The syringe filter may be made of stainless material, and it is possible to effectively pulverize adipose tissue by securing sufficient strength. In addition, each of the first to third filters may be a filter bag, which is a closed bag-shaped filter kit made of a flexible plastic material, may be in the form where an inlet is provided on one side and an outlet is provided on the other side and the interior space is partitioned. In the case of using a filter bag, adipose tissue may be pulverized by injecting adipose tissue into the filter bag and passing it through the filter by applying external pressure (for example, pressure using a tool such as a silicone spatula).

According to one embodiment of the present invention, step a1) may be to pulverize the adipose tissue by passing the adipose tissue at least twice through each filter. Specifically, the first to third filters are syringe filters, and after mounting syringes at both ends, the piston movement of the syringe is repeated to pulverize the extracted adipose tissue.

According to one embodiment of the present invention, step a1) may include a first pulverizing step of passing the extracted adipose tissue back and forth at least twice through a first filter having a pore diameter 2 mm to 5 mm, specifically 2 mm to 4 mm or 2 mm to 3 mm. In the first pulverizing step, the extracted adipose tissue may be pulverized by passing it through the first filter 2 to 7 times, or 2 to 3 times. In addition, the first pulverizing step may include removing the residue that did not pass through the first filter. The residue removed in the first pulverizing step may be fibers in adipose tissue. The fibers may interfere with the pulverization of adipose tissue using the second and third filters, and may also inhibit the activity of the tissue regeneration patch, so it is preferable to remove them.

According to one embodiment of the present invention, step a1) may include a second pulverizing step of passing the adipose tissue that has been through the first filter back and forth at least twice through a second filter having a pore diameter of 400 μm to 800 μm. In the second pulverizing step, the adipose tissue pulverized through the first filter may be pulverized by passing it through the second filter 2 to 7 times, or 2 to 3 times. In addition, the second pulverizing step may include removing the residue that did not pass through the second filter.

According to one embodiment of the present invention, step a1) may include a third pulverizing step of passing the adipose tissue pulverized through the second filter back and forth at least twice through a second filter having a pore diameter of 150 μm to 250 μm. In the third pulverizing step, the adipose tissue pulverized through the second filter may be pulverized by passing it through the third filter 2 to 7 times, or 2 to 3 times. In addition, the third pulverizing step may include removing the residue that did not pass through the third filter.

According to one embodiment of the present invention, step a1) can stepwise pulverize adipose tissue using a filter having a small pore diameter as described above, greatly shortening the time for finely pulverizing adipose tissue, and maintaining the high cellular activity of the cells in the adipose tissue extract. Specifically, when step a1) is used, there is an advantage in that a large amount of adipose tissue and active cells and active proteins effective for effective treatment can be secured in spite of the fine pulverization of the adipose tissue by a physical method. Furthermore, when step a1) is used, it is possible to collect the extracellular matrix and growth factors in an optimally active state, and also to have physical properties capable of performing (3D) bioprinting.

According to one embodiment of the present invention, Step A) may further include a step a2) of mixing the adipose tissue micronized by the third filter with physiological saline and allowing it to stand to allow phase separation into an aqueous phase layer and an organic phase layer, followed by removal of the aqueous layer. Through this, it is possible to remove cells, adipose tissue, blood, physiological saline, etc. that are excessively finely pulverized and have poor cell activity, which may interfere with the activity of the final tissue regeneration patch intended in the present invention. Through this, it is possible to obtain an adipose tissue-derived extracellular matrix containing a large amount of factors that can effectively help cell differentiation.

According to one embodiment of the present invention, step A) may further include a3) passing the adipose tissue micronized by the third filter through a fourth filter having a pore diameter of 25 μm to 125 μm, followed by removing the filtrate and collecting the residue collected in the fourth filter. Specifically, after filtering the adipose tissue micronized by the third filter through the fourth filter, the filtered material may be discarded to obtain a material collected in the filter. Specifically, step a3) may be a step of mixing the adipose tissue micronized through step a1) with physiological saline, followed by filtration using the fourth filter to separate and remove the material to be filtered, and then using the material collected in the fourth filter as a micronized adipose tissue extract. The material to be filtered and removed may include cells, adipose tissue, blood, physiological saline, etc. that are excessively finely pulverized and thus have poor cell activity. Through this, it is possible to obtain a higher purity adipose tissue-derived extracellular matrix.

Step B): Injecting the Micronized Adipose Tissue Extract into a Mold of a Predetermined Shape According to one embodiment of the present invention, the mold of the predetermined shape may be a 2D or 3D shape corresponding to the area of damaged or lost tissue. Specifically, the mold of the predetermined shape can be manufactured using a portable device such as a mobile phone camera, a tablet camera, or the like to obtain two-dimensional data on a damaged or lost tissue area of a patient and then using the information converted into three-dimensional image information on the damaged or missing tissue area. In addition, the mold of the predetermined shape may be manufactured using 3D data on an area of damaged or lost tissue in a patient using 3D scanner equipment commonly available in the art. The mold of the predetermined shape may be formed of sidewalls having open upper and lower portions. Through this, the adipose tissue extract injected into the mold can be effectively cooled and solidified.

Based on the information thus obtained about the area of the damaged or lost tissue of the patient, a 3D mold corresponding to the area of the damaged or lost tissue may be manufactured using 3D printing equipment. As for the 3D printer, a 3D printer available in the art may be used. Furthermore, the mold can make it possible for the injected (or applied) adipose tissue to maintain the three-dimensional form specific to the affected area (i.e., three-dimensional form such as shape, size, depth, etc.), and the mold may be removed once the tissue regeneration patch is manufactured. The mold may be formed using a biocompatible polymer generally used in the art. Specifically, the mold may be manufactured using PCL. Since the PCL has a low melting point and high flexibility, there is an advantage in that it can be easily separated from the manufactured tissue regeneration patch. Furthermore, PCL can enable fabrication of an optimal mold conforming to the three-dimensional shape of the affected area, and a tissue regeneration patch manufactured using a mold having a shape substantially the same as the three-dimensional shape of an affected area can effectively adhere to the affected area to assist in recovery.

According to one embodiment of the present invention, when the adipose tissue extract is injected into the mold, in addition to the adipose tissue extract, a bioactive factor that can help tissue regeneration may also be injected.

Step C): Cooling the Mold into which the Adipose Tissue Extract is Injected at a Temperature Range Between −25° C. and −10° C.

According to one embodiment of the present invention, step C) may be to cool and freeze the adipose tissue extract injected into the mold to solidify it.

According to one embodiment of the present invention, step C) may be performed on a cooling plate at a temperature between −25° C. and −10° C. The cooling plate may be controlled in the temperature range to freeze the adipose tissue extract injected into the mold. The temperature of the frozen adipose tissue extract may be substantially equivalent to the temperature of the cooling plate.

According to one embodiment of the present invention, the mold into which the adipose tissue extract is injected may be positioned on a polyurethane film provided on the cooling plate. Specifically, the mold has an open top and bottom, and the injected adipose tissue extract may be solidified into a tissue regeneration patch while in direct contact with the cooling plate. In this case, the cooling plate and the tissue regeneration patch may not come off or the tissue regeneration patch may be damaged in the process of removing the tissue regeneration patch. In order to prevent this, the polyurethane film is provided on the cooling plate, and the adipose tissue extract is applied on the polyurethane film, so that the tissue regeneration patch can be easily removed after cooling. That is, the polyurethane film may serve as a release film.

Step D): Removing the Mold to Obtain a Tissue Regeneration Patch.

According to one embodiment of the present invention, step D) may be to separate the mold from the tissue regeneration patch in which the adipose tissue extract is solidified through cooling. The tissue regeneration patch thus obtained is solidified in a form suitable for close contact with the affected area, and further has the advantage of easy handling during application to the affected area.

After the tissue regeneration patch manufactured as described above is attached to the affected area, it can be fixed with a dressing bandage or the like to recover the affected area.

According to one embodiment of the present invention, steps B) to D) may be performed in a bioprinter equipped with a cooling plate under a sterile atmosphere. Specifically, the mold formation, injection and cooling of the adipose tissue extract may be performed in a bioprinter that is controlled to be blocked from the external environment and maintains the internal space in a sterile state. In the case of using such a bioprinter, problems such as inflow of impurities and infection in the manufacturing process of the tissue regeneration patch can be minimized.

According to one embodiment of the present invention, the thickness of the tissue regeneration patch may be at least 1 mm. Specifically, when the thickness of the tissue regeneration patch is less than 1 mm, tissue cells are not regenerated, so the recovery of the affected area may be delayed or the surface of the tissue to be restored may become non-uniform. More specifically, the thickness of the tissue regeneration patch may be 1 mm to 10 mm, 2 mm to 7 mm, or 2 mm to 5 mm.

According to one embodiment of the present invention, the tissue regeneration patch may be for treating lost or damaged tissue in a human or animal. Specifically, the tissue regeneration patch may be for treating lost or damaged skin tissue, and may target the human body or an animal. More specifically, the tissue regeneration patch may be for treatment of damaged skin tissue according to diabetic foot disease. In addition, the tissue regeneration patch may be for the treatment of skin tissue damaged by burns. The treatment of the skin tissue may include recovery of lost skin tissue or regeneration of damaged skin tissue.

Hereinafter, an example will be given to describe the present invention in detail. However, the example according to the present invention may be modified into various other forms, and the scope of the present invention is not to be construed as being limited to the embodiment described below. The example of the present specification is provided to explain the present invention more completely to those of ordinary skill in the art.

Example 1

After adipose tissue was collected from Otsuka Long-Evans Tokushima fatty (OLETF) diabetic model mice using liposuction, and then left for about 5 minutes, adipose tissue was obtained by settling saline and blood mixed with adipose tissue to remove the precipitate. Then, the syringe containing the adipose tissue and a new syringe were mounted at the bidirectional inlet of the connector with a stainless syringe filter (Adnizer, SKT-AN-2400, BSL) with a pore diameter of about 2.4 mm, and the adipose tissue was allowed to be pulverized through the filter two to three times with the piston movement, followed by removal of the fibers that did not pass through the filter. Thereafter, the adipose tissue from which the fibers were removed was pulverized sequentially using a syringe filter with a pore diameter of about 500 μm and a syringe filter with a pore diameter of about 200 μm, and the residue that did not pass through the filters was removed. Next, a process of mixing the pulverized adipose tissue with physiological saline and allowing the mixture to stand to remove the aqueous layer including cells and blood was performed twice, thereby obtaining a micronized adipose tissue extract.

After removing the skin tissue on the back of the OLETF diabetic model mouse, a mold matching the shape of the removed skin tissue was placed on a cooling plate in a 3D bioprinter (Dr. INVIVO, ROKIT Healthcare), and the micronized adipose tissue extract was injected into the mold using the 3D bioprinter. The temperature of the cooling plate was set to about −15° C., and the micronized adipose tissue extract was frozen to manufacture a tissue regeneration patch.

After attaching the manufactured tissue regeneration patch to the affected area of the OLETF diabetic model mouse, a dressing was applied.

FIG. 1 is a set of photographs sequentially showing the manufacturing process of the tissue regeneration patch according to the embodiment and application of the tissue regeneration patch to the affected area.

Comparative Example 1

The skin tissue of the back region of the OLETF diabetic model mouse in Example 1 was removed and only the dressing was applied.

Comparative Example 2

After removing the skin tissue on the back of the OLETF diabetic model mouse in Example 1, the micronized adipose tissue extract prepared as in Example 1 was directly applied to the affected area and a dressing was applied.

For the size (area) of the affected area on the 3rd, 7th, and 12th days after dressing in Example 1 and Comparative Examples 1 and 2, it was measured using Image J (National Institutes of Health, Rockville, MA), and the graphed results are shown in FIG. 2. In FIG. 2, Comparative Example 1 is indicated as "Wound only", Comparative Example 2 is indicated as "Fat, RT", and Example 1 is indicated as "Fat, −15° C.". According to the results of FIG. 2, in the case of Example 1, compared to Comparative Examples 1 and 2, it was confirmed that the size of the area of the affected area recovered faster. Specifically, the average value of the area of the affected area recovered in Comparative Example 1 was 71.7%, the average value of the area of the area recovered in Comparative Example 2 was 82.3%, and the average value of the area of the recovered area in Example 1 was 94.6%. In the case of Example 1, it exhibited about 23% higher recovery of the affected area compared to Comparative Example 1 without additional treatment, and about 13% higher recovery of the affected area compared to Comparative Example 2 to which the simply pulverized adipose tissue extract was applied.

Furthermore, the angiogenesis effect of Example 1 and Comparative Examples 1 and 2 was investigated through CD31 immunohistochemical staining. Specifically, the three sites with the highest vascular density were selected from the affected area on the 12th day after the dressing treatment, and the number of blood vessels was counted in a 400-fold field of view under an optical microscope to obtain an average value for each field of view. At this time, blood vessels with a large diameter that can accommodate 6-8 red blood cells and blood vessels with thick muscle layer were excluded. A single vascular endothelial cell or a subpopulation of endothelial cells without a lumen was calculated by considering each group as one blood vessel.

FIG. 3 shows the results of neovascularization in the recovered affected area in Example 1, Comparative Examples 1 and 2; In FIG. 3, Comparative Example 1 is indicated as "Wound only", Comparative Example 2 is indicated as "Fat, RT", Example 1 is indicated as "Fat, −15° C.", and neovascularization is indicated by arrows. Furthermore, FIG. 4 is a graph of the result of FIG. 3. Specifically, as for the number of microvessels, an average of 10 (±1) in Comparative Example 1, 11.6 (±2.4) in Comparative Example 2, and 30.3 (±2.7) in Example 1 were observed per 400-fold optical microscope field of view, and the difference between each group was statistically significant (p<0.05). According to FIGS. 3 and 4, in Comparative Example 2 and Example 1 in which the autologous adipose tissue extract was applied, it was confirmed that new blood vessels were well observed compared to Comparative Example 1. Furthermore, in the case of Example 1 in which the adipose tissue extract was manufactured into a tissue regeneration patch for the affected area and applied, compared to Comparative Example 1 in which the adipose tissue extract was directly applied, it may confirmed that more than twice as many new blood vessels were observed, and the recovery of the skin tissue was greatly improved.

Reference Example

A tissue regeneration patch was manufactured in the same manner as in Example 1, but the temperature of the cooling plate was set to −20° C.

FIG. 5 is an image of a tissue regeneration sheet according to a Reference Example observed using a scanning electron microscope. According to FIG. 5, in the case of Example 1 frozen at −15° C., it was confirmed that the adipose form was similar to the adipose form of the control at 0° C., and in the case of the Reference Example frozen at −20° C., it was confirmed that the form was significantly different. As a result of the experiment, when the amount of adipose change in the tissue regeneration patch is relatively small, the recovery force of the affected area is high, so it was confirmed that it is preferable to set the temperature of the cooling plate within the range of −10° C. to −20° C.

The invention claimed is:

1. A method of manufacturing a tissue regeneration patch, comprising:
   A) preparing a micronized adipose tissue extract;
   B) injecting the micronized adipose tissue extract into a mold of a predetermined shape;
   C) cooling the mold into which the adipose tissue extract is injected at a temperature of more than −20° C. and less than −10° C.; and
   D) removing the mold to obtain a tissue regeneration patch, wherein step A) comprises the step of pulverizing an adipose tissue in stages sequentially using a1) a first filter having a pore diameter of 2 mm to 5 mm, a second filter having a pore diameter of 400 μm to 800 μm, and a third filter having a pore diameter of 150 μm to 250 μm.

2. The method according to claim 1, wherein further comprising the step of a2) mixing the adipose tissue micronized by the third filter with physiological saline and leaving the mixture to stand, and after phase separation into an aqueous phase layer and an organic phase layer, removing the aqueous phase layer.

3. The method according to claim 1, wherein in step a1), the adipose tissue is pulverized by repeatedly passing the adipose tissue back and forth through each filter.

4. The method according to claim 1, wherein the adipose tissue is autologous adipose tissue.

5. The method according to claim 1, wherein the mold of the predetermined shape is a 2D or 3D shape corresponding to an area of damaged or lost tissue.

6. The method according to claim 1, wherein the step C) is performed on a cooling plate at a temperature of more than −20° C. and less than −10° C.

7. The method according to claim 6, wherein the mold into which the adipose tissue extract is injected is positioned on a polyurethane film provided on the cooling plate.

8. The method according to claim 1, wherein the steps B) to D) are performed in a bioprinter equipped with a cooling plate under a sterile atmosphere.

9. The method according to claim 1, wherein the thickness of the tissue regeneration patch is at least 1 mm.

10. The method according to claim 1, wherein the tissue regeneration patch is for treating damaged or lost skin tissue.

* * * * *